United States Patent

Schmitt

[11] Patent Number: 6,090,137
[45] Date of Patent: Jul. 18, 2000

[54] SOLID WOVEN TUBULAR PROSTHESIS METHODS

[75] Inventor: Peter J. Schmitt, Garnerville, N.Y.

[73] Assignee: Meadox Medicals, Inc., Oakland, N.J.

[21] Appl. No.: 09/245,164

[22] Filed: Feb. 5, 1999

Related U.S. Application Data

[63] Continuation of application No. 08/546,560, Oct. 20, 1995, Pat. No. 5,913,894, which is a continuation of application No. 08/349,439, Dec. 5, 1994, abandoned, which is a division of application No. 08/052,657, Apr. 26, 1993, Pat. No. 5,370,682.

[51] Int. Cl.$^7$ ............................................. A61F 2/04
[52] U.S. Cl. .................. 623/1.44; 623/1.51; 623/901; 139/387 R; 139/410
[58] Field of Search .................. 623/1, 11, 1.44, 623/1.51, 901; 139/387 R, 410

[56] References Cited

U.S. PATENT DOCUMENTS

| | | |
|---|---|---|
| 161,272 | 3/1875 | Reed . |
| 200,965 | 3/1878 | Baker . |
| 299,017 | 5/1884 | Schenck et al. . |
| 299,018 | 5/1884 | Schenck et al. . |
| 348,698 | 9/1886 | Sibley . |
| 427,929 | 5/1890 | Stowe . |
| 486,620 | 11/1892 | Stowe . |
| 532,902 | 1/1895 | Palmer . |
| 610,463 | 9/1898 | Stowe . |
| 697,390 | 4/1902 | Beck . |
| 697,391 | 4/1902 | Beck et al. . |
| 697,392 | 4/1902 | Beck et al. . |
| 899,092 | 9/1908 | Alvord . |
| 1,164,304 | 12/1915 | Nicewarner . |
| 2,025,039 | 12/1935 | Cannon . |
| 2,978,787 | 4/1961 | Liebig . |
| 3,000,076 | 9/1961 | Runton et al. . |
| 3,095,017 | 6/1963 | Bleiler et al. . |
| 3,105,492 | 10/1963 | Jeckel . |
| 3,272,204 | 9/1966 | Artandi et al. . |
| 3,316,557 | 5/1967 | Liebig . |
| 3,317,924 | 5/1967 | LeVeen . |
| 4,025,684 | 5/1977 | Neidhardt . |
| 4,086,941 | 5/1978 | Thompson . |
| 4,193,137 | 3/1980 | Heck . |
| 4,312,261 | 1/1982 | Florentine . |
| 4,346,741 | 8/1982 | Banos et al. . |
| 4,416,028 | 11/1983 | Eriksson et al. . |
| 4,441,215 | 4/1984 | Kaster . |
| 4,670,286 | 6/1987 | Nyilas et al. . |
| 4,719,837 | 1/1988 | McConnell et al. . |
| 4,728,329 | 3/1988 | Mansat . |
| 4,743,250 | 5/1988 | Kitagawa et al. . |
| 4,834,747 | 5/1989 | Gogolewski . |
| 4,834,755 | 5/1989 | Silvestrini et al. . |

(List continued on next page.)

FOREIGN PATENT DOCUMENTS

| | | |
|---|---|---|
| 0 117 072 A1 | 8/1984 | European Pat. Off. . |
| 0 317 408 A1 | 5/1989 | European Pat. Off. . |
| 0 452 807 A3 | 9/1991 | European Pat. Off. . |
| 0 493 788 A1 | 7/1992 | European Pat. Off. . |
| 0 501 890 A1 | 9/1992 | European Pat. Off. . |
| 2548225 A1 | 1/1985 | France . |
| 2583072 A1 | 12/1986 | France . |
| WO 87/05796 | 10/1987 | WIPO . |
| WO 88/00813 | 2/1988 | WIPO . |
| WO 90/12550 | 11/1990 | WIPO . |
| WO 91/10766 | 7/1991 | WIPO . |

OTHER PUBLICATIONS

R.T. Brown, "Three–Dimensional Braiding", *Handbook of Industrial Braiding* (undated).

Atkins & Pearce, *Formation of Industrial Braids*, pp. 3.1–3.12 (undated).

*Primary Examiner*—Paul Prebilic
*Attorney, Agent, or Firm*—Hoffmann & Baron, LLP

[57] ABSTRACT

A solid woven tubular prosthesis having sufficient inherent wall stiffness so as to be radially self-supporting. The solid woven prosthesis is capable of being formed with a smooth, continuous inner wall that improves the hemodynamic flow with respect to conventional woven prosthesis, thereby facilitating the flow of fluid therethrough.

8 Claims, 3 Drawing Sheets

U.S. PATENT DOCUMENTS

| | | |
|---|---|---|
| 4,917,699 | 4/1990 | Chervitz . |
| 4,917,700 | 4/1990 | Aikins . |
| 4,923,470 | 5/1990 | Dumican . |
| 4,975,262 | 12/1990 | Suto et al. . |
| 5,084,065 | 1/1992 | Weldon et al. .............................. 623/1 |
| 5,091,246 | 2/1992 | Yasui et al. . |
| 5,116,360 | 5/1992 | Pinchuk et al. . |
| 5,178,630 | 1/1993 | Schmitt . |
| 5,273,080 | 12/1993 | Morohashi et al. . |
| 5,282,848 | 2/1994 | Schmitt ....................................... 623/1 |
| 5,354,329 | 10/1994 | Whalen . |
| 5,357,839 | 10/1994 | Brookstein et al. . |
| 5,413,597 | 5/1995 | Krajicek . |
| 5,913,894 | 6/1999 | Schmitt .................................. 623/1.51 |

SOLID WOVEN TUBULAR PROSTHESIS METHODS

This application is a continuation of Ser. No. 08/546,560 filed Oct. 20, 1995 and now U.S. Pat. No. 5,913,894 which is a continuation of Ser. No. 08/349,439 filed Dec. 5, 1994 and now abandoned which is a divisional of Ser. No. 08/052,657 filed Apr. 26, 1993 and now U.S. Pat. No. 5,370,682.

BACKGROUND OF THE INVENTION

The present invention relates to tubular prostheses, and, more particularly, to woven tubular prostheses having increased wall stiffness.

In the past, tubular prostheses have commonly been manufactured by, for example, weaving a plurality of warp yarns and a plurality of fill yarns into a tubular fabric. Such products, however, typically lack sufficient radial stiffness to maintain an open lumen, i.e., if unsupported, they will radially collapse. The tendency to radially collapse or kink is particularly problematic to a surgeon during implantation of the prosthesis.

Conventional weaves used for vascular grafts and other medical devices are known as simple weaves, i.e., one-ply weaves. These types of constructions are inherently strong with respect to burst pressure, but suffer from the above-mentioned kinking and collapsing tendencies, as well as the tendency to ravel at the ends, making it difficult to properly hold sutures. Additionally, the one-ply structure has inherent limitations as to the properties which can be engineered into the final woven product. For example, simple weaves do not stretch well radially or longitudinally and, further, possess only a simple pore structure due to the single layer.

To overcome these characteristics, prior art prostheses are typically crimped at equidistant lengths along their longitudinal axis. The crimping is believed to provide the prosthesis with sufficient radial stiffness to maintain an open lumen. The crimping additionally provides a degree of longitudinal compliance to the prosthesis.

Crimping, however, is not without its disadvantages. For example, the crimps create a plurality of irregularities along the inner wall of the prosthesis that may create blood flow disturbances. These blood flow disturbances become more pronounced and consequently less acceptable as the diameter of the prosthesis is reduced. In addition, thrombi can accumulate in the valleys of the crimps, tending to form hyperplastic pockets.

An alternative prior art technique for providing radial stiffness to a woven prosthesis involves the use of a stiffening component. Specifically, the fabric is woven around a suitable stiffener or, alternatively, such a stiffener is secured to either the interior or exterior of the prosthesis following weaving. The use of a stiffener, however, creates its own drawbacks. For example, tissue ingrowth may be hindered by the stiffener, the porosity of the prosthesis may be affected by the stiffener and, finally, the ability to suture the prostheses to the host vessel may be hindered by the stiffener.

It would therefore be desirable to provide a woven tubular prosthesis that contains sufficient inherent wall stiffness so as to be radially self-supporting. Such a graft would not require crimping or the use of stiffening components, thereby providing a smooth, continuous inner wall that better simulates the natural hemodynamics of the connecting vessels, even with respect to those prostheses having a relatively small diameter, e.g., down to about 4 mm. Additionally, the same prosthesis would be less prone to pinching, kinking or other collapsing tendencies when subjected to bending forces, as well as being resistant to ravelling when cut to size during surgery. The prosthesis would also have the ability to hold sutures well. Finally, the pore structure would be more tortuous, thereby providing better hemostasis at the time of implantation and the ability to support long term healing and tissue incorporation.

SUMMARY OF THE INVENTION

The present invention relates to implantable multi-ply woven tubular prostheses, such as vascular grafts, intraluminal devices, such as endoprostheses, and the like. The prosthetic devices of the present invention are fabricated from a multi-ply solid weave construction which inherently provides increased radial strength over traditional simple one-ply weave patterns. The multi-ply solid weaves are characterized in that the woven fabric has a plurality of superposed plies including a plurality of circumferentially extending fill yarns and a plurality of longitudinally extending warp yarns. The warp or fill yarns must continuously pass through at least two adjacent plies. That is, at least two adjacent layers must have common yarns which serve to interlock and integrate the plies into a unitary structure.

Due to the potential for using materials having different characteristics for each ply, a variety of structural and property gradients can be achieved. For example, a porosity gradient from the innermost to the outermost ply can be incorporated into the prosthesis, thereby reducing blood loss yet, at the same time, encouraging tissue ingrowth and assimilation of the prosthesis into the body. For example, the outer ply can exhibit a porosity greater than the porosity exhibited by the inner ply. Similarly, different types of yarns may be used in the interlocking plies to achieve a gradient of properties such as stiffness, compliance, texture, ravel resistance and fray resistance. This can be achieved by using, for example, different yarns or by subjecting the same or different yarns to different treatments prior to incorporation into the fabric. In one embodiment, elastomeric yarns are incorporated, in an elongated state, into the prosthesis in the warp direction such that subsequent to the weaving process the fabric will retract longitudinally, thereby providing longitudinal compliance. Other means of providing longitudinal compliance, such as heat-setting techniques, are also contemplated.

The implantable prosthetic devices of the present invention may be used in a variety of locations in the body, such as intraluminal applications in the vascular system, pulmonary system or gastrointestinal track. Of particular usefulness, however, are vascular grafts that are implanted surgically or by endoscopic means.

DETAILED DESCRIPTION OF THE INVENTION

As mentioned above, weaving is commonly employed to fabricate tubular prostheses. Woven prostheses are ideal in that they provide strong, pressure-resistant vessels. These same grafts, however, typically require radial support through mechanical treatment, such as crimping, or through the incorporation of radial stiffening yarns.

Figure 1:
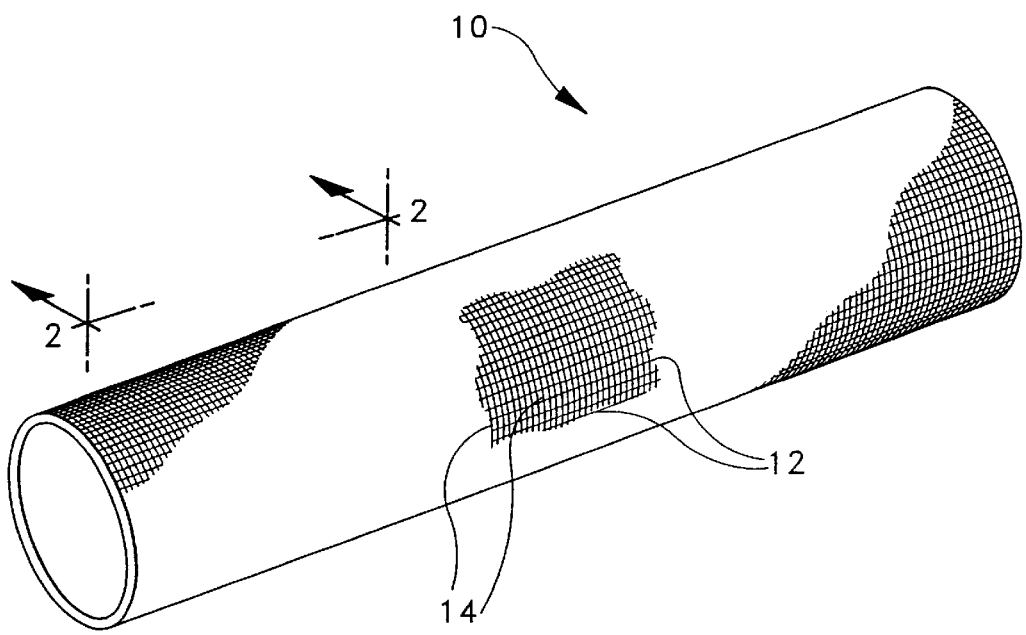
FIG. 1 is a perspective view of a solid woven tubular prosthesis.

Referring to FIG. 1, a woven tubular prosthesis 10 fabricated in accordance with the present invention is shown. As illustrated, the prosthesis may include longitudinally-extending warp yarns 12 and circumferentially-extending fill yarns 14. The prosthesis of the present invention differs from prior art woven prostheses (which typically were formed with simple, one ply weaves) in that the present prosthesis includes a plurality of solid woven plies (i.e., the plies are not separable into discrete layers).

The use of several plies allows certain ideal characteristics to be designed into the prosthesis. Specifically, different yarns can be used in the different plies. For example, depending on the chosen materials, a porosity gradient can be created in the wall of the prosthesis. Such a gradient resists leaking of fluid from the inner wall, yet still allows ingrowth of natural tissue into the outer wall. Moreover, because the prosthesis is a solid woven unitary structure, the discretely-designed plies are interconnected in such a fashion that the plies become inseparable and also, at the same time, provide sufficient inherent wall stiffness to the prostheses to allow it to be radially self-supporting.

Figure 2:
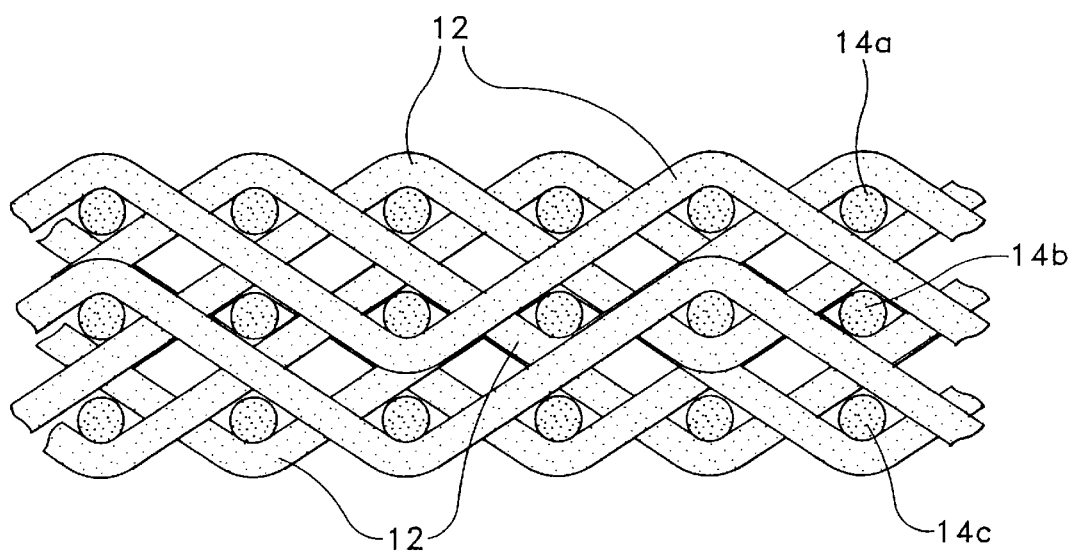
FIG. 2 is a cross-sectional view taken along lines 2—2 of FIG. 1.

The solid woven prosthesis of the present invention can best be understood by reference to FIG. 2, which depicts a prosthesis having three plies. Referring to FIG. 2a, fill yarn 14a is located in the outermost ply, fill yarn 14b is located in the intermediate ply and fill yarn 14c is located in the innermost ply. A plurality of warp yarns 12 are solidly woven throughout these fill yarns.

Specifically, by definition each warp yarn (or fill yarn) in a solid woven prosthesis must pass continuously through, and therefore be part of, at least two adjacent plies. Of course, the design of the prosthesis may require that each warp yarn pass continuously through each and every ply. In such a case, all of the plies will have warp yarns in common to form a unitary solid structure.

In a preferred embodiment (as best shown in FIGS. 2–2a), the prosthesis is fabricated with three plies. The outermost ply preferably contains textured or filamentous materials for enhanced tissue attachment. The intermediate ply preferably contains a fusible material to aid in ravel resistance. Finally, the innermost ply preferably contains a bioresorbable material to aid in healing, long term patency and zero preclotting. Such designs, i.e., those having different properties and property gradients, cannot be created with simple, single-ply weaves as found in the prior art and conventionally employed in medical devices of this sort.

The solid woven prosthesis of the present invention has a wall thickness greater than that of the typical prior art device, thereby providing a degree of radial support. For example, wall thicknesses may range from 0.50 mm to 1.25 mm, whereas a conventional wall thickness ranges from 0.25 mm to 0.50 mm. Moreover, the solid woven design provides greater wall stiffness and resistance to kinking or pinching, as compared to single-ply grafts due to the increased wall thickness. Notwithstanding the increased wall thickness of the multi-ply unitary construction, excellent longitudinal or axial flexibility for handling is retained. Specifically, tubular products made from this weave structure are sufficiently flexible and compliant to meet the requirements of a prosthetic implant or graft.

Because the solid woven prosthesis is radially self-supporting, crimping or the use of stiffeners is not required. As a result, the inner wall of the prosthesis can be fabricated as a smooth, continuous surface. In contrast, the inner wall of a conventional crimped one-ply prosthesis includes a plurality of irregularities or corrugations that disturb the flow of fluid therethrough, e.g., the flow of blood through an artery. This is additionally problematic because debris may collect in these irregularities causing further complications in patients with arterial disease. In larger-sized prostheses, these disturbances have little effect on the flow of fluid. However, as the diameter of the prostheses decreases, the acceptability of the disturbances decreases. The present invention, by providing a prostheses having a smooth, continuous inner wall, overcomes this disadvantage associated with the prior art and, as a result, is capable of being employed to fabricate relatively small-sized prostheses.

Figure 3:
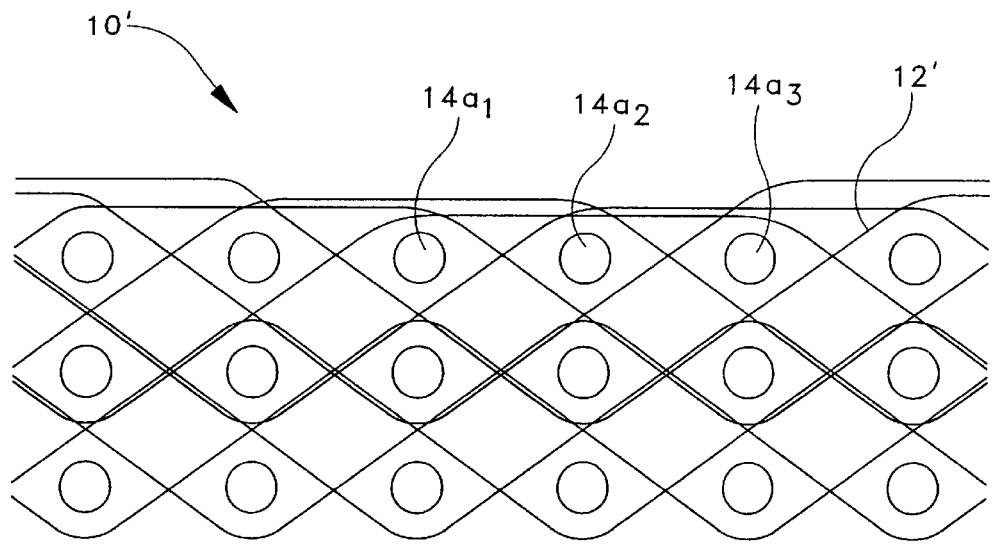
FIG. 3 is a cross-sectional view similar to FIG. 2 wherein each of the outermost warp yarns float over three fill yarns.
Figure 3A:
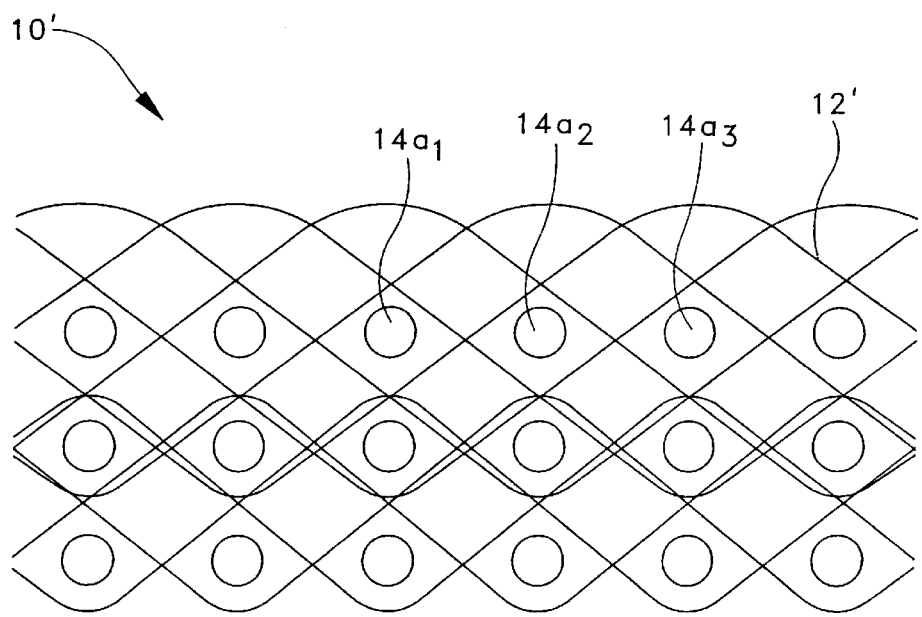
FIG. 3a depicts the prostheses of FIG. 3 after a heat-setting process in which the outermost warp yarns form a raised filamentous velour surface.
Figure 4:
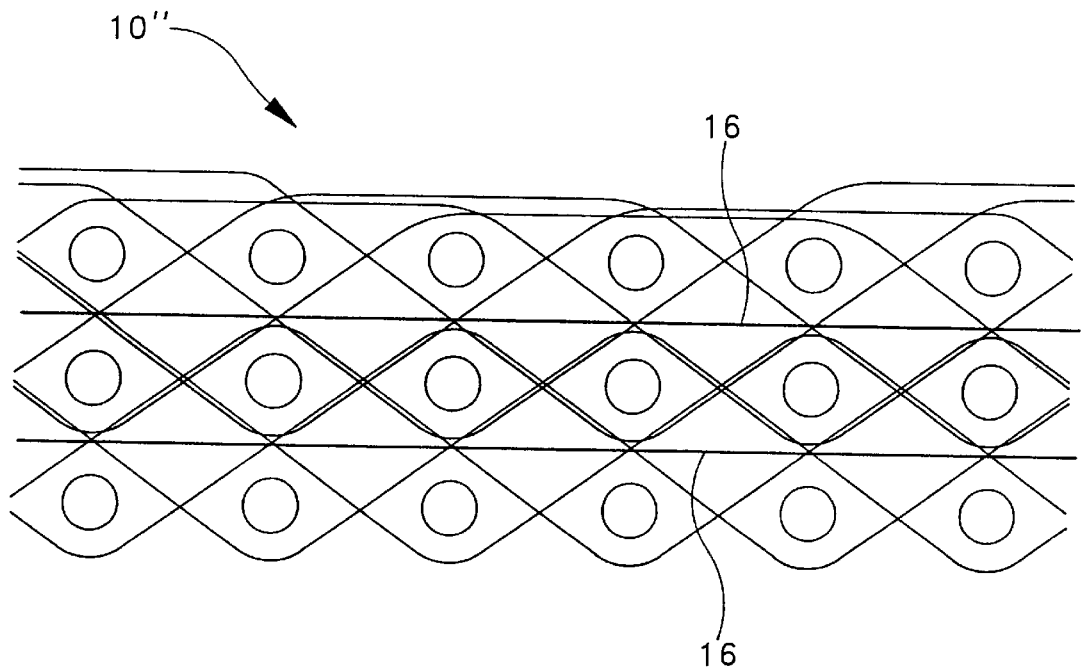
FIG. 4 is a cross-sectional view similar to FIG. 2 wherein a pair of elastomeric warp yarns have been incorporated into the prostheses.
Figure 4A:
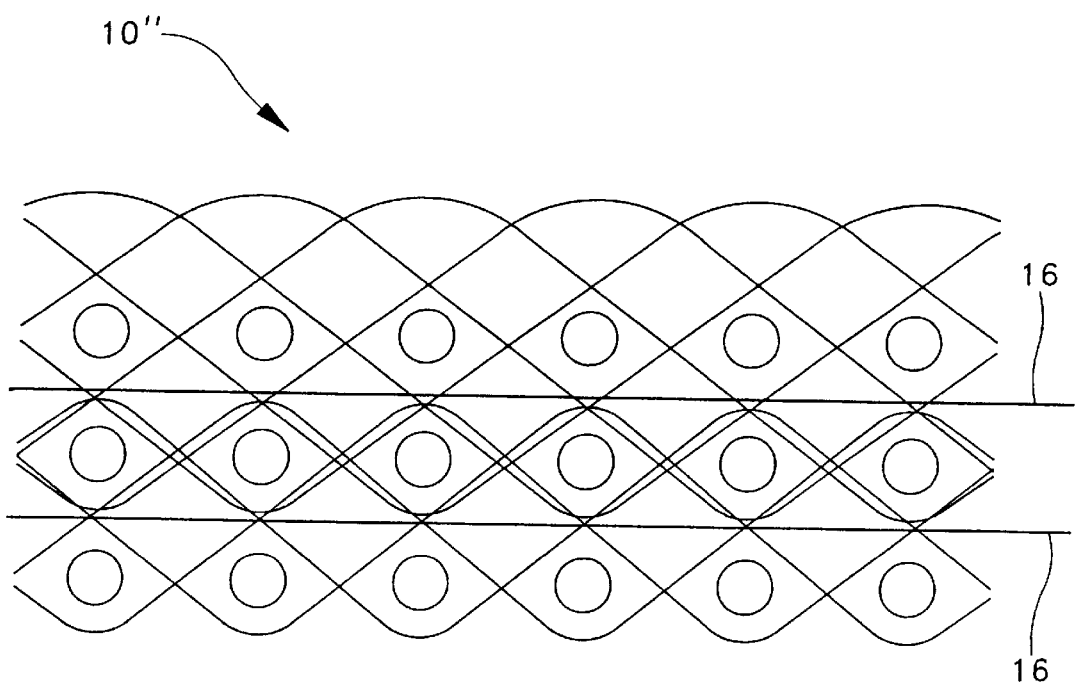
FIG. 4a depicts the prostheses of FIG. 4 after a heat-setting process wherein the outermost warp yarns form a raised filamentous velour surface.

As described below in Example 3, a solid woven texturized graft having raised velour loops can be fabricated in accordance with the present invention. Specifically, with reference to FIG. 3, prosthesis 10' is woven such that the warp yarns located at the outer-most surface pass externally over at least two fill yarns. For example, warp yarn 12' passes over fill yarns $14a_1$, $14a_2$ and $14a_3$. The "loose" surface weave allows these warp yarns to rise from the surface following heat-setting, thereby forming a filamentous velour surface as shown in FIG. 3a.

In an additional embodiment, as described below in Example 4, at least one elastomeric warp yarn 16 is incorporated into the fabric. Prosthesis 10" is woven with the elastomeric warp yarns in a stretched state such that subsequent to weaving the fabric will longitudinally retract, thereby providing a degree of longitudinal compliance. Longitudinal compliance assists the surgeon in sizing the length of the prosthesis for implantation and also provides a degree of flexibility to the prosthesis following implantation.

Following manufacture and treatment, the prosthesis is sealed in a package. The package, along with the prosthesis contained therein, is then subjected to a sterilization procedure, e.g., a radiation procedure, a heat procedure, etc. Alternately, the prosthesis may be sterilized prior to being sealed in its packaging or may be sterilized by the physician performing the implant operation at the time of such surgery.

EXAMPLES

Examples of polymeric materials useful in the present invention include, without limitation, yarns made from polyester, polypropylene, polytetrafluoroethylene, polyethylene, polyurethane and resorbable polymers.

The following examples serve to provide further appreciation of the invention but are not meant in any way to restrict the effective scope of the invention.

Example 1–3 Ply Solid Woven

The following specifications are used to fabricate a solid woven prosthesis of the present invention.

| | |
|---|---|
| Weave | 3 Ply Solid Woven (Triple Plain), tubular |
| Warp Yarn | Textured 50 denier/48 filament polyester |
| Fill Yarn | 2 ply/textured 50 denier/48 filament polyester |
| Ends per inch | 160 |
| Picks per inch | 200 |

Subsequent to weaving the prosthesis, the material is scoured in a basic solution of warm water (e.g., 150° F.) and cleaning detergent. It is then rinsed to remove the cleaning agents. Next, the prosthesis is heat-set on mandrels of the final desired inside diameter. Typically, the outside diameter of the mandrel is approximately equal to the diameter of the final prosthesis. The woven tubing is woven to be 5–15% oversize so that it can be mounted onto a mandrel and shrink fitted to an exact diameter. Heat-setting can take place in a steam heated autoclave at about 250° F. for about 5–10 minutes or in a convection oven at 250–400° F. for about 10–30 minutes.

Example 2–3 Ply Solid Woven with Longitudinal Compliance

The following specifications are used to fabricate a solid woven prosthesis of the present invention.

| | |
|---|---|
| Weave | 3 Ply Solid Woven (Triple Plain), tubular |
| Warp Yarn | Textured 50 denier/48 filament polyester |
| Fill Yarn | 2 ply/textured 50 denier/48 filament polyester |
| Ends per inch | 160 |
| Picks per inch | 160 |

Subsequent to weaving the prosthesis, the material is scoured in a basic solution of warm water (e.g., 150° F.) and cleaning detergent. It is then rinsed to remove the cleaning agents. Next, the prosthesis is heat-set on mandrels of the final desired inside diameter. Typically, the outside diameter of the mandrel is equal to the diameter of the final prosthesis. The woven tubing is woven to be 5–15% oversize so that it can be mounted onto a mandrel and shrink fitted to an exact diameter.

Heat-setting can take place in a steam heated auto-clave at about 250° F. for about 5–10 minutes or in a convection oven at 250–400° F. for about 10–30 minutes. The heat-setting can be done in a two-step process. The first step involves heat-setting the prosthesis in its fully extended state to shrink fit the prosthesis snugly to the mandrel. The second heat-setting step entails compressing the prosthesis longitudinally. The compression is on the order of 25–50%. The prosthesis is then heat-set a second time using at least the same conditions as in the first heat-setting cycle.

As a result of the heat-setting, the warp yarns buckle and crimp. The heat locks the yarns in this geometry to build in "spring like" or elastomeric properties.

Example 3–3 Ply Solid Woven with Longitudinal Compliance and External Velour The following specifications are used to fabricate a solid woven prosthesis of the present invention.

| | |
|---|---|
| Weave | 3 Ply Solid Woven, Tubular with 3 filling floats on outer ply |
| Warp Yarn | Textured 50 denier/48 filament polyester |
| Fill Yarn | 2 ply/textured 50 denier/48 filament polyester |
| Ends per inch | 160 |
| Picks per inch | 160 |

Subsequent to weaving the prosthesis, the material is scoured in a basic solution of warm water (e.g., 150° F.) and cleaning detergent. It is then rinsed to remove the cleaning agents. Next, the prosthesis is heat-set on mandrels of the final desired inside diameter. Typically, the outside diameter of the mandrel is equal to the diameter of the final prosthesis. The woven tubing is woven to be 5–15% oversize so that it can be mounted onto a mandrel and shrink fitted to an exact diameter.

Heat-setting can take place in a steam heated autoclave at about 250° F. for about 5–10 minutes or in a convection oven at 250–400° for about 10–30 minutes. The heat-setting can be done in a two-step process. The first step involves heat-setting the prosthesis in its fully extended state to shrink fit the prosthesis snugly to the mandrel. The second heat-setting step entails compressing the prosthesis longitudinally. The compression is on the order of 25–50%. The prosthesis is then heat-set a second time using at least the same conditions as in the first heat-setting cycle.

As a result of the heat-setting, the warp yarns buckle and crimp. The heat locks the yarns in this geometry to build in "spring like" properties. The warp yarns in the outer ply which are floating over 3 picks, would raise from the fabric, forming a filamentous velour surface.

Example 4–3 Ply Solid Woven with Elastomeric Components to Provide Longitudinal Compliance The following specifications are used to fabricate a solid woven prosthesis of the present invention.

| | |
|---|---|
| Weave | 3 Ply Solid Woven, Tubular with 3 filling floats on outer ply |
| Warp Yarn | Textured 50 denier/48 filament polyester & 140 denier Lycra Spandex |
| Fill Yarn | 2 ply/textured 50 denier/48 filament polyester |
| Ends per inch | 160 of polyester, 20 of spandex |
| Picks per inch | 160 |

The tubing is woven to include an elastomeric yarn in the warp direction, such as Lycra Spandex from DuPont. The elastomeric yarn is woven into the fabric by inserting it between the first and second plies. The elastomeric yarn is woven in a stretched state, so that after weaving the fabric will retract longitudinally. The elastomeric yarn provides the longitudinal compliance to the graft.

Subsequent to weaving the prosthesis, the material is scoured in a basic solution of warm water (e.g., 150° F.) and cleaning detergent. It is then rinsed to remove the cleaning agents. The scouring process allows the woven tubing to fully retract by relieving the stress induced by weaving the elastomeric warp yarns in a stressed state.

The prosthesis is heat-set on mandrels of the final desired inside diameter. Typically, the outside diameter of the mandrel is equal to the diameter of the final prostheses. The tubing is woven to be 5–15% over-size so that it can be mounted onto a mandrel and shrink fitted to an exact diameter. Heat-setting can take place in a steam heated autoclave at about 250° F. for about 5–10 minutes or in a convection oven at 250–400° F. for about 10–30 minutes.

The warp yarns in the outer ply which are floating over 3 picks, are raised from the fabric, forming a filamentous velour surface. Longitudinal compliance on the order of 25–50% can be achieved by this method.

Thus, while there have been described what are presently believed to be the preferred embodiments of the invention, those skilled in the art will realize that various changes and modifications may be made to the invention without departing from the spirit of the invention, and it is intended to claim all such changes and modifications which fall within the scope of the invention.

What is claimed is:

1. A method for weaving a tubular prosthesis, comprising:
   providing a plurality of warp biocompatible implantable yarns and a plurality of fill biocompatible implantable yarns; and
   weaving at least two superposed plies, each of said plies having a plurality of circumferentially extending fill yarns and a plurality of longitudinally extending warp yarns such that each of the yarns extending in either the circumferential or longitudinal direction continuously passes through at least two adjacent plies of yarns to interlock or integrate an outer ply and an inner ply of said prosthesis;
   wherein said outer ply exhibits a porosity greater than the porosity exhibited by said inner ply.

2. The method according to claim 1, further comprising the step of heat-setting said prosthesis whereby said prosthesis undergoes a period of controlled shrinkage.

3. The method according to claim 2, wherein said prosthesis is heat-set in an elastically compressed position to provide said prosthesis with a degree of longitudinal compliance.

4. The method according to claim 3, wherein said plies are formed from non-homogeneous materials whereby the physical properties of said outer ply differ from the physical properties of said inner ply.

5. The method according to claim 4, further comprising a middle ply, and wherein said outer ply is formed from a filamentous material for enhanced tissue attachment, said middle ply is formed from a fusible material to aid in ravel resistance, and said inner ply is formed from a bioresorbable material to aid in healing.

6. The method according to claim 1, wherein said prosthesis is formed with a smooth continuous inner surface to facilitate flow of fluid therethrough.

7. A method according to claim 1, wherein said warp yarns are formed from a substantially elastic material to provide said prosthesis with a degree of longitudinal compliance.

8. A method for repairing a tubular vessel in a patient's body, comprising:
   removing a damaged portion of said tubular vessel from said patient's body;
   providing a biocompatible implantable solid woven tubular prosthesis having at least two superposed plies, each of said plies having a plurality of circumferentially extending fill yarns and a plurality of longitudinally extending warp yarns such that each of the yarns extending in either the circumferential or longitudinal direction continuously passes through at least two adjacent plies of yarns to interlock or integrate an outer ply and an inner ply of said prosthesis, wherein said prosthesis is sized to substantially match the length and diameter of said damaged portion;
   positioning said prosthesis into the region of said vessel from which said damaged portion was removed; and
   securing each end of said prosthesis to a respective end of said vessel whereby a continuous fluid pathway is reestablished along said vessel.

* * * * *